(12) United States Patent
Richardson

(10) Patent No.: US 10,758,261 B2
(45) Date of Patent: Sep. 1, 2020

(54) MICRODERMABRASION SYSTEMS AND RELATED TECHNOLOGIES

(71) Applicant: LCL Enterprises, Inc., Everett, WA (US)

(72) Inventor: Patrick Richardson, Everett, WA (US)

(73) Assignee: LCL Enterprises, Inc., Everett, WA (US)

( * ) Notice: Subject to any disclaimer, the term of this patent is extended or adjusted under 35 U.S.C. 154(b) by 197 days.

(21) Appl. No.: 15/821,610

(22) Filed: Nov. 22, 2017

(65) Prior Publication Data

US 2018/0140317 A1 May 24, 2018

Related U.S. Application Data

(60) Provisional application No. 62/426,165, filed on Nov. 23, 2016, provisional application No. 62/453,934, filed on Feb. 2, 2017.

(51) Int. Cl.
*A61B 17/3205* (2006.01)
*A61B 17/30* (2006.01)
(Continued)

(52) U.S. Cl.
CPC .......... *A61B 17/3205* (2013.01); *A61B 17/30* (2013.01); *A61B 17/54* (2013.01);
(Continued)

(58) Field of Classification Search
CPC ..... A61B 17/3205; A61B 17/30; A61B 17/54; A61B 2017/320004; A61B 2017/306; A61B 2217/005; A61B 2017/00477; A61B 18/14; A61B 2017/00747; A61B 2017/00876; A61B 2017/00473; A61B 2017/308; A61B 2017/320008; A61B 2018/0047; A61B 2018/00291; A61M 35/003; A61H 7/002; A61H 23/004;
(Continued)

(56) References Cited

U.S. PATENT DOCUMENTS 2,701,559 A 2/1955 Cooper
2,712,823 A * 7/1955 Kurtin .................. A61B 17/322
606/131
(Continued)

FOREIGN PATENT DOCUMENTS

KR 10-2012-0031716 A 4/2012
WO 2015136116 9/2015

OTHER PUBLICATIONS

International Search Report and Written Opinion of counterpart International Application No. PCT/US2017/063141; dated Mar. 12, 2018; 13 pages.

*Primary Examiner* — Phong Son H Dang
(74) *Attorney, Agent, or Firm* — Perkins Coie LLP

(57) ABSTRACT

Skin treatment systems, handpieces, suction wands, and methods of treatment are disclosed herein. A skin treatment system includes a treatment handpiece with removable tips, a console unit, and a suction assembly. The console unit can have a pressurization device configured to be fluidically coupled to the suction assembly. The suction assembly is configured to hold a subject's skin while the treatment handpiece moves along the epidermis. The tips can replaced any number of times to perform during a treatment session.

16 Claims, 12 Drawing Sheets

(51) Int. Cl.
| | |
|---|---|
| *A61M 35/00* | (2006.01) |
| *A61H 7/00* | (2006.01) |
| *A61H 23/00* | (2006.01) |
| *A61N 7/00* | (2006.01) |
| *A61B 17/54* | (2006.01) |
| *A61H 23/02* | (2006.01) |
| *A61B 17/00* | (2006.01) |
| *A61B 17/32* | (2006.01) |
| *A61B 18/00* | (2006.01) |
| *A61B 18/14* | (2006.01) |

(52) U.S. Cl.
CPC ........... *A61H 7/002* (2013.01); *A61H 23/004* (2013.01); *A61H 23/02* (2013.01); *A61M 35/003* (2013.01); *A61N 7/00* (2013.01); *A61B 18/14* (2013.01); *A61B 2017/00473* (2013.01); *A61B 2017/00477* (2013.01); *A61B 2017/00747* (2013.01); *A61B 2017/00876* (2013.01); *A61B 2017/306* (2013.01); *A61B 2017/308* (2013.01); *A61B 2017/320004* (2013.01); *A61B 2017/320008* (2013.01); *A61B 2018/0047* (2013.01); *A61B 2018/00291* (2013.01); *A61B 2217/005* (2013.01); *A61H 2201/0207* (2013.01); *A61H 2201/0214* (2013.01); *A61H 2201/0242* (2013.01); *A61H 2201/0285* (2013.01); *A61H 2201/10* (2013.01); *A61H 2201/5061* (2013.01); *A61H 2230/505* (2013.01)

(58) Field of Classification Search
CPC ............ A61H 23/02; A61H 2201/5061; A61H 2201/0285; A61H 2201/0207; A61H 2201/0214; A61H 2201/0242; A61H 2230/505; A61H 2201/10; A61N 7/00
See application file for complete search history.

(56) References Cited

U.S. PATENT DOCUMENTS

| | | | | |
|---|---|---|---|---|
| 2,867,214 | A * | 1/1959 | Wilson | A61B 17/54 606/131 |
| 2,881,763 | A | 4/1959 | Robbins | |
| 2,921,585 | A | 1/1960 | Schumann | |
| 3,214,869 | A | 11/1965 | Stryker | |
| 3,964,212 | A | 6/1976 | Karden | |
| 4,378,804 | A | 4/1983 | Cortese, Jr. | |
| 4,957,747 | A | 9/1990 | Stiefel | |
| 5,012,797 | A | 5/1991 | Liang et al. | |
| 5,037,431 | A | 8/1991 | Summers et al. | |
| 5,037,432 | A | 8/1991 | Molinari | |
| 5,100,412 | A | 3/1992 | Rosso | |
| 5,122,153 | A | 6/1992 | Harrel | |
| 5,207,234 | A | 5/1993 | Rosso | |
| 5,800,446 | A | 9/1998 | Banuchi | |
| 5,810,842 | A | 9/1998 | Di Fiore et al. | |
| 5,882,201 | A | 3/1999 | Salem | |
| 5,971,999 | A | 10/1999 | Naldoni | |
| 6,042,552 | A | 3/2000 | Cornier | |
| 6,241,739 | B1 | 6/2001 | Waldron | |
| 6,423,078 | B1 | 7/2002 | Bays et al. | |
| 6,641,591 | B1 * | 11/2003 | Shadduck | A61B 17/545 606/131 |
| 6,730,098 | B2 | 5/2004 | Chang | |
| 7,354,423 | B2 * | 4/2008 | Zelickson | A45D 26/0004 604/289 |
| 7,384,405 | B2 * | 6/2008 | Rhoades | A45D 24/007 601/15 |
| 7,572,238 | B2 * | 8/2009 | Rhoades | A45D 34/041 601/138 |
| 8,372,086 | B2 * | 2/2013 | Lind | A61B 17/54 132/75.6 |
| 8,945,104 | B2 * | 2/2015 | Boone, III | A61H 9/0057 606/9 |
| 9,080,267 | B2 * | 7/2015 | Batchvarova | D04H 11/08 |
| 9,138,257 | B2 * | 9/2015 | Revivo | A61B 17/54 |
| 9,486,615 | B2 * | 11/2016 | Ignon | A61B 17/54 |
| D845,496 | S * | 4/2019 | Cole | D24/200 |
| 2004/0010268 | A1 * | 1/2004 | Gabehart | A61B 17/54 606/131 |
| 2004/0193079 | A1 * | 9/2004 | Siddhartha | A61H 19/44 601/72 |
| 2004/0236291 | A1 * | 11/2004 | Zelickson | A45D 26/0004 604/289 |
| 2004/0249320 | A1 * | 12/2004 | Yamazaki | A45D 34/042 601/46 |
| 2005/0038448 | A1 | 2/2005 | Chung | |
| 2006/0058714 | A1 * | 3/2006 | Rhoades | A61M 35/003 601/73 |
| 2007/0123808 | A1 * | 5/2007 | Rhoades | A61H 33/14 601/73 |
| 2007/0156124 | A1 * | 7/2007 | Ignon | A61M 35/003 606/9 |
| 2009/0124985 | A1 * | 5/2009 | Hasenoehrl | A45D 34/04 604/289 |
| 2009/0157094 | A1 * | 6/2009 | Yeshurun | A61B 17/54 606/131 |
| 2009/0177171 | A1 * | 7/2009 | Ignon | A61B 17/54 604/289 |
| 2010/0049177 | A1 * | 2/2010 | Boone, III | A61H 9/0057 606/9 |
| 2011/0270274 | A1 * | 11/2011 | Hull, Jr. | A45D 34/04 606/131 |
| 2012/0165710 | A1 * | 6/2012 | Nichols | A61H 7/005 601/72 |
| 2013/0096577 | A1 | 4/2013 | Shadduck | |
| 2013/0138119 | A1 * | 5/2013 | Luzon | A61B 17/54 606/131 |
| 2013/0158547 | A1 * | 6/2013 | David | A61B 18/14 606/41 |
| 2013/0204238 | A1 * | 8/2013 | Lederman | A61B 18/203 606/9 |
| 2013/0274762 | A1 * | 10/2013 | Guay | A45D 44/22 606/131 |
| 2014/0202493 | A1 * | 7/2014 | Zelickson | A46B 13/02 15/22.1 |
| 2014/0276469 | A1 * | 9/2014 | Greep | A61C 1/141 604/264 |
| 2014/0330289 | A1 * | 11/2014 | Revivo | A61B 17/54 606/131 |
| 2014/0343481 | A1 * | 11/2014 | Ignon | A61M 5/3298 604/21 |
| 2015/0051620 | A1 * | 2/2015 | Presser | A61B 17/54 606/131 |
| 2015/0080667 | A1 * | 3/2015 | Bahr | A61M 1/0023 600/249 |
| 2015/0290442 | A1 | 10/2015 | Ignon et al. | |
| 2016/0008031 | A1 | 1/2016 | Beijens et al. | |
| 2016/0166273 | A1 * | 6/2016 | Levy | B26B 7/00 606/131 |
| 2017/0014145 | A1 * | 1/2017 | Favie | A61B 17/54 |
| 2017/0304654 | A1 * | 10/2017 | Blanche | A61B 18/18 |
| 2018/0014855 | A1 * | 1/2018 | Beijens | A61B 17/54 |
| 2018/0110538 | A1 * | 4/2018 | Bailar | A61B 17/54 |
| 2018/0235662 | A1 * | 8/2018 | Horton | A61B 17/54 |

* cited by examiner

MICRODERMABRASION SYSTEMS AND RELATED TECHNOLOGIES

CROSS-REFERENCE TO RELATED APPLICATIONS

This application claims the benefit of U.S. Provisional Patent Application No. 62/426,165, filed Nov. 23, 2016, and U.S. Patent Application No. 62/453,934, filed Feb. 2, 2017, which are incorporated by reference in their entireties.

TECHNICAL FIELD

The present disclosure relates generally to systems for treating skin. In particular, several embodiments are directed to skin treatment systems, handpieces, tissue-tissue holders, suction wands, and methods of treatment.

BACKGROUND

Conventional microdermabrasion procedures exfoliate skin to improve the appearance of skin, remove skin abnormalities, and otherwise treat skin. Conventional microdermabrasion equipment can deliver a flow of crystals (e.g., aluminum oxide or alumina crystals) to abrade the epidermis. A vacuum pump compressor draws the crystals through a conduit and into a hollow handpiece held against a patient's skin. The crystals then strike the epidermis to abrade the skin. The crystals are removed via a suction tube connected to the handpiece. The crystals are then collected in a container. Unfortunately, it may be difficult to adjust the level of abrasion, crystals can clog lines, and crystals can damage equipment components, such as flow lines. Other conventional vacuum-based handpieces have abrasive rings at one end of a hollow tube. Vacuum pumps provide a low pressure to draw the patient's skin against the abrasive ring. Dislodged skin cells, which are located within an opening defined by the abrasive ring, are drawn through the hollow tube via the vacuum. It is difficult to manually control the level of pressure applied to the skin because of the constant vacuum, thereby making it difficult to control the level of abrasion. If the vacuum level is too high, the patient can experience painful abrasion of the skin.

SUMMARY

At least some embodiments are systems that include a treatment handpiece, removable tips, a console unit, and a suction assembly. The console unit can have a pressurization device configured to be fluidically coupled to the suction assembly. The suction assembly is configured to hold a subject's skin while the treatment handpiece moves along the epidermis. In some embodiments, the handpiece is a wand capable of being manually applied to a patient. The tips can be replaced and can be configured to perform microdermabrasion, dermabrasion, or other desired procedures. The tips can be interchanged at any time to provide a wide range of different treatments. In a treatment session, a single handpiece can be used with an array of tips for a custom treatment. In some embodiments, the pressurization device can include one or more vacuum sources (e.g., pumps). In one embodiment, the handpiece can include a vacuumless wand that enables a user to accurately control the applied pressure. For example, user can manually press the handpiece against the subject's skin to accurately vary the applied pressure to increase or decrease the level of abrasion. Some procedures may involve a separate vacuum device, such as a vacuum wand, for performing post treatment procedures. Post treatment procedures can include, without limitation, removing dislodged or dead cells, massaging, cleaning, and/or otherwise affecting the treatment site.

In some embodiments, a treatment handpiece includes a double-ended solid core wand with ends that receive abrasive elements. The wand can have a one-piece or multi-piece construction and can be made, in whole or in part, of metal, plastic, or other rigid materials. The wand can have an ergonomic design to provide a comfortable grip. In some embodiments, the abrasive elements can be replaced to provide different levels of abrasion. In some procedures, a single wand can be used throughout the entire treatment session. Alternatively, multiple wands can be used in one or more treatment sessions to limit the number of times tips are changed. The abrasive elements can be scrapers, tips, or heads permanently or detachably coupled to the wand.

In further embodiments, abrasive elements can include an abrasive material, such as diamond, aluminum oxide, sand, silicon carbide, and/or silicon oxide. The abrasive material (e.g., particles, crystals, abrasive grit, etc.) can be coupled to (e.g., adhered, bonded, etc.) or integrated into the body of the element. For example, abrasive material of about 60 grit (average particle size less than 254 µm), 80 grit (average particle size less than 165 µm), 100 grit (average particle size less than 122 µm), 120 grit (average particle size less than 102 µm), 150 grit (average particle size less than 89 µm), or 200 grit (average particle size less than 70 µm) or the like can be adhered to a surface of the element. The grit sizes can be based on ASTM standards. In some embodiments, one abrasive tip has first abrasive particles having an average diameter less than a first diameter, and second abrasive tip has abrasive particles having an average diameter greater than the second diameter. A ratio of the first diameter to the second diameter can be less than 0.3, 0.4, 0.5, 0.6, 0.7, and 0.9. Abrasive material can include, without limitation, diamond crystals, aluminum oxide crystals, etc. In some embodiments, aluminum oxide of about 100 grit can remove a relatively large amount of cells to provide an aggressive treatment, and aluminum oxide of about 150 grit can remove a relatively low amount of cells. In other embodiments, the abrasive elements can have a textured surface formed via machining, stamping, etching, or the like.

In some embodiments, a microdermabrasion system includes a microdermabrasion wand, a console unit, and a suction assembly. The microdermabrasion wand has a first abrasive tip, a second abrasive tip, and a wand body. The console unit includes a wand holder and a pressurization device. The pressurization device can be configured to provide a low pressure. The suction assembly can include a suction wand and a conduit connecting the suction wand to the pressurization device. The suction assembly can be configured to hold the subject's skin while the microdermabrasion wand moves along the subject's skin. In some procedures, a head of the suction wand can remain generally stationary to hold the subject's tissue while the microdermabrasion wand is moved repeatedly back and forth along a treatment site. Operation of the pressurization device can be controlled to provide a desired level of suction. After achieving the desired level of microdermabrasion, the suction wand can be moved along a treatment site to collect dead cells, dislodge cells, and/or to clean the site.

The suction wand can be configured to draw sufficient vacuum to hold the subject's skin. In aggressive microdermabrasion treatments, a strong vacuum can be used. The handpiece can be moved rapidly along the skin while a significant amount of pressure is applied. For mild microdermabrasion, a relatively weak vacuum can be used to comfortably hold the subject's skin. The pressurization device can include, without limitation, one or more vacuum sources, pumps, regulators, valves, filters, connectors, hoses, or other fluidic components.

The abrasive elements or tips are configured to be detachably coupled to opposing ends of the wand body. In some embodiments, the abrasive tips are threadably coupled to respective ends of the wand body. The microdermabrasion system, in some embodiments, can include a wide array of different abrasive tips. The wand body can have an elongated configuration and can have a handle portion between its ends. In one embodiment, the handle portion has a substantially solid cross-section along most of or all of its longitudinal length.

The microdermabrasion wand can be used to alternatingly abrade the subject's skin using multiple installed abrasive tips. In removable tip embodiments, the microdermabrasion wand has a main body with first and second ends. The first abrasive tip can be removed from the first end of the main body, and another abrasive tip can be attached to the main body. The abrasive tips can be replaced any number of times during one or more treatment sessions.

In some embodiments, a microdermabrasion system includes a microdermabrasion wand, a console, and a skin holder assembly. The microdermabrasion wand having a first abrasive tip, a second abrasive tip, and a wand body extending between the first and second abrasive tips. The console unit includes a wand holder and a pressurization device. The skin holder assembly including a suction wand and a conduit connecting the suction wand to the pressurization device. The pressurization device is configured to draw a sufficient vacuum to cause the suction wand to hold a subject's skin to inhibit movement of skin contacting the first abrasive tip while the microdermabrasion wand moves relative to the suction wand.

In yet other embodiments, a microdermabrasion system includes a microdermabrasion wand and a console unit. The microdermabrasion wand has a first abrasive tip, a second abrasive tip, and a wand body extending between the first and second abrasive tips. The console unit includes a wand holder and a pressurization device configured to draw a vacuum. The system can further include a skin holder assembly having a suction wand and a conduit connecting the suction wand to the pressurization device. The pressurization device is configured to draw a sufficient vacuum to cause the suction wand to hold a subject's skin to inhibit movement of skin while the first abrasive tip moves along the skin. For example, the suction wand can remain stationary with respect to an area of the subject's skin exposed to suction.

In some embodiments, a method comprises applying a vacuum skin holder wand to a subject's skin. The subject's skin is treated using a microdermabrasion wand while the vacuum skin holder wand holds the subject's skin. The microdermabrasion wand is configured to move along the subject's skin while the vacuum wand remains generally stationary. In one embodiment, the vacuum wand and microdermabrasion wand are held in the user's hands. Additionally or alternatively, the vacuum wand can be used for pre- or post-treatment procedures, including massaging, cleaning, etc.

In another embodiment, a method includes sequentially exfoliating the subject's skin using a first abrasive tip and a second abrasive tip of a microdermabrasion wand while the first and second tips are concurrently coupled to a main body of the microdermabrasion wand. After sequentially abrading the skin, the first abrasive tip can be replaced with a third abrasive tip. The subject's skin can be sequentially exfoliated using the second and third abrasive tips, which are concurrently coupled to the wand body.

In yet other embodiments, a method for treating a subject includes applying a skin holding wand to the subjects skin. The skin holding wand can be a vacuum wand or a vacuumless wand. After the skin holding wand securely holds the subject's tissue, the subject's skin can be abraded using an abrasive tip of a microdermabrasion wand can abrade the skin while the skin holding one inhibits movement of the skin. In some embodiments, the skin holding wand is configured to be held in one hand of the user while the microdermabrasion wand is held in the user's other hand.

The subject's skin can be sequentially abraded using different tips installed on a wand body of the microdermabrasion wand. The abrasive tips can be replaced with additional tips to provide treatment. In one procedure, the subject's skin is alternatingly abraded using two abrasive tips detachably coupled to opposite ends of an elongated microdermabrasion wand. A user can switch between the different abrasive tips while the abrasive tips remain concurrently coupled to a wand body. The abrasive tips can have roughened surface areas that are different from one another and can have different abrasion characteristics. In vacuumless abrasion procedures, the microdermabrasion wand is pressed against the subject skin to control the level of abrasion. Optionally, a skin holder can be used with the vacuumless microderm abrasion wand. In one procedure, a vacuum skin holding device can hold the subject's skin via a vacuum while the vacuumless microdermabrasion wand is used to perform the procedure.

At least some of the embodiments disclosed herein can be for cosmetically beneficial treatments. As such, some treatment procedures may be for the sole purpose of altering a site to conform to a cosmetically desirable appearance, texture, or other desirable cosmetic characteristic or feature. Cosmetic procedures can be performed without providing any or minimal therapeutic effect. For example, some treatment procedures may be directed to cosmetic goals, such as smoother skin, that do not include restoration of health, physical integrity, or the physical well-being of a subject. Some example methods can target areas with a large number of dead or old skin cells to improve the area's appearance. Procedures can also reduce or eliminate fine lines, wrinkles (e.g., smile lines, crow's feet, etc.), scars, stretch marks, and/or uneven pigmentation (e.g., age spots). Cosmetic methods can be administered by a non-medically trained person.

BRIEF DESCRIPTION OF THE DRAWINGS

Many aspects of the technology can be better understood with reference to the following drawings. Identical reference numbers identify similar elements or acts. The sizes and relative positions of elements in the drawings are not necessarily drawn to scale.

DETAILED DESCRIPTION

The present disclosure describes systems for performing skin treatments. Several of the details set forth below are provided to describe the following examples and methods in a manner sufficient to enable a person skilled in the relevant art to practice, make, and use them. Various aspects of the technology are directed to abrading, roughening, cleaning, smoothing, or otherwise altering tissue (e.g., a layer of tissue, the surface of tissue, etc.) to improve one or more skin characteristics. In some procedures, the system can be used to perform a wide range of different types of microdermabrasion procedures to remove skin cells (e.g., dead and/or old skin cells) to, for example, improve the skin's appearance, treat acne, or the like. Several of the details and advantages described below, however, may not be necessary to practice certain examples and methods of the technology. Additionally, the technology may include other examples and methods that are within the scope of the technology but are not described in detail.

References throughout this specification to "one example," "an example," "one embodiment," or "an embodiment" mean that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. The headings provided herein are for convenience only and are not intended to limit or interpret the scope or meaning of the technology.

Figure 1:
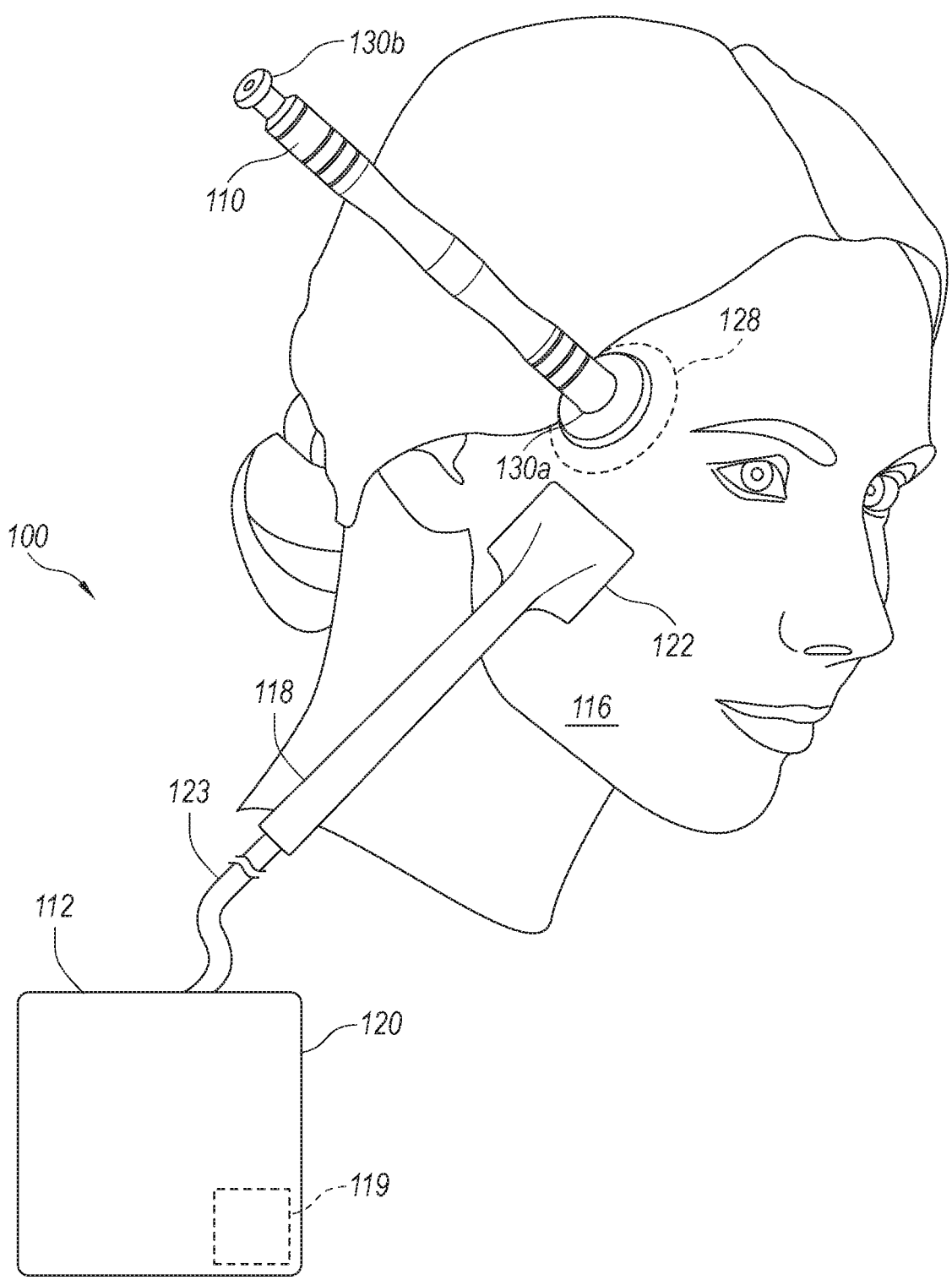
FIG. 1 shows a microdermabrasion system treating a subject's face in accordance with an embodiment of the technology.

FIG. 1 shows a microdermabrasion system 100 in accordance with an embodiment of the technology. The microdermabrasion system 100 can include a treatment handpiece in the form of a microdermabrasion wand 110. The microdermabrasion wand 110 can be pressed against and moved along the subject's skin 116. Each end of the microdermabrasion wand 110 can carry a respective replaceable abrasive tip 130a, 130b. The user can alternate between the abrasive tips 130a, 130b. The tips 130a, 130b can be interchanged or replaced with other tips to achieve the desired microdermabrasion treatment.

The microdermabrasion system 100 can further include a skin holder assembly or vacuum apparatus 112 ("vacuum apparatus 112"). The vacuum apparatus 112 can include a vacuum skin holder wand or suction wand 118 ("vacuum skin holder wand 118"), a console unit 120, and a conduit 123. A head 122 of the vacuum wand 118 can be applied to the subject's skin 116 to limit, inhibit, or substantially prevent movement of skin at the treatment site 128 (indicated in phantom line). The vacuum wand 118 can be hollow and can connect to the conduit 123 (e.g., a vacuum hose or line) to provide gentle suction to hold the subject's skin, remove dead skin or cells, clean the skin surface, massage tissue, or otherwise altering the skin. The console unit 120 can include a pressurization device 119 in fluid communication with the conduit 123. The pressurization device 119 can include, without limitation, one or more vacuum sources, regulators, controllers, pressure sensors, combinations thereof, or the like.

During treatment, the user's hand can hold the wand 110 while the user's other hand can hold the vacuum wand 118. The vacuum wand 118 can hold the skin taut while the microdermabrasion wand 110 is gently moved across the skin. The console unit 120 can be operated to control the applied vacuum level.

Figure 2B:
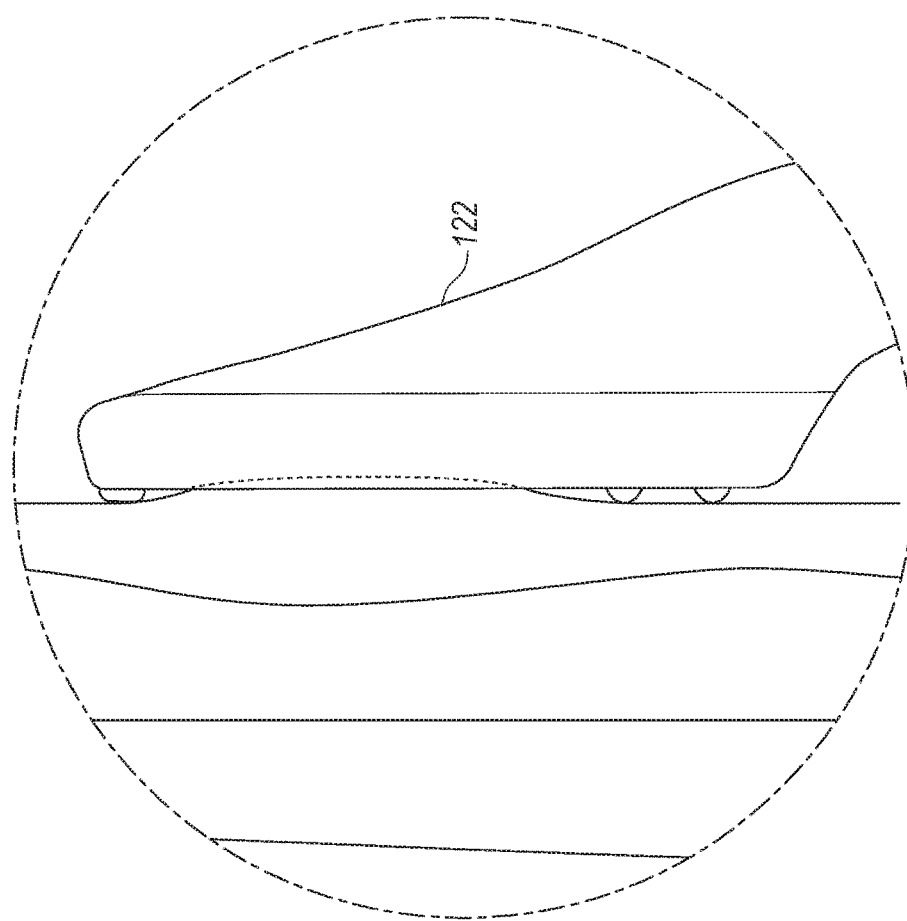
FIG. 2B is a detailed view of the interface between a suction wand and the subject's skin.
Figure 2A:
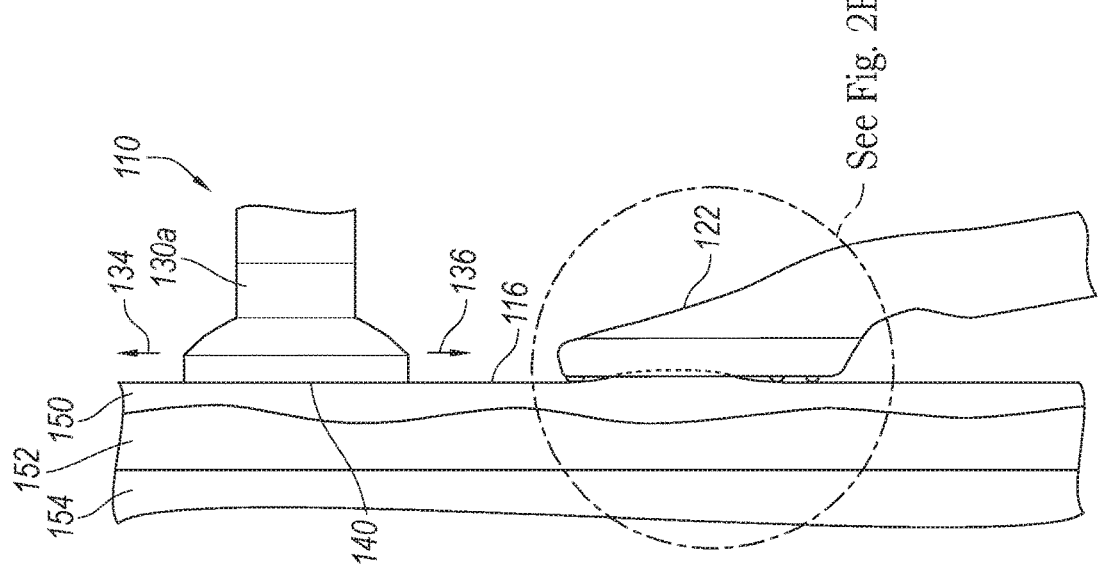
FIG. 2A is a schematic cross-sectional view of the subject's skin, dermis, and subcutaneous tissue.

FIG. 2A is a schematic cross-sectional view of the subject's skin, dermis, and subcutaneous tissue. FIG. 2B is an enlarged detailed view of the head 122 applied to the subject's skin. Referring now to FIG. 2A, the abrasive tip 130a can be moved, as indicated by arrows 134, 136, along the skin 116. The abrasive tip 130a can include a contact region 140 configured to exfoliate, abrade, scrap, and/or roughen the epidermis 150 with or without affecting underlying tissue (e.g., the dermis 152 and/or subcutaneous tissue 154). For example, the applied pressure can be kept below a threshold level that would cause damage to the dermis 152 and/or subcutaneous tissue 154. The head 122 can remain generally stationary to hold the skin 116 while the wand 110 is moved back and forth. After treating an area, the head 122 can be slid over or placed on the treated area to remove dislodged tissue, remove dead cells, clean skin, massage tissue, or the like.

Figure 3:
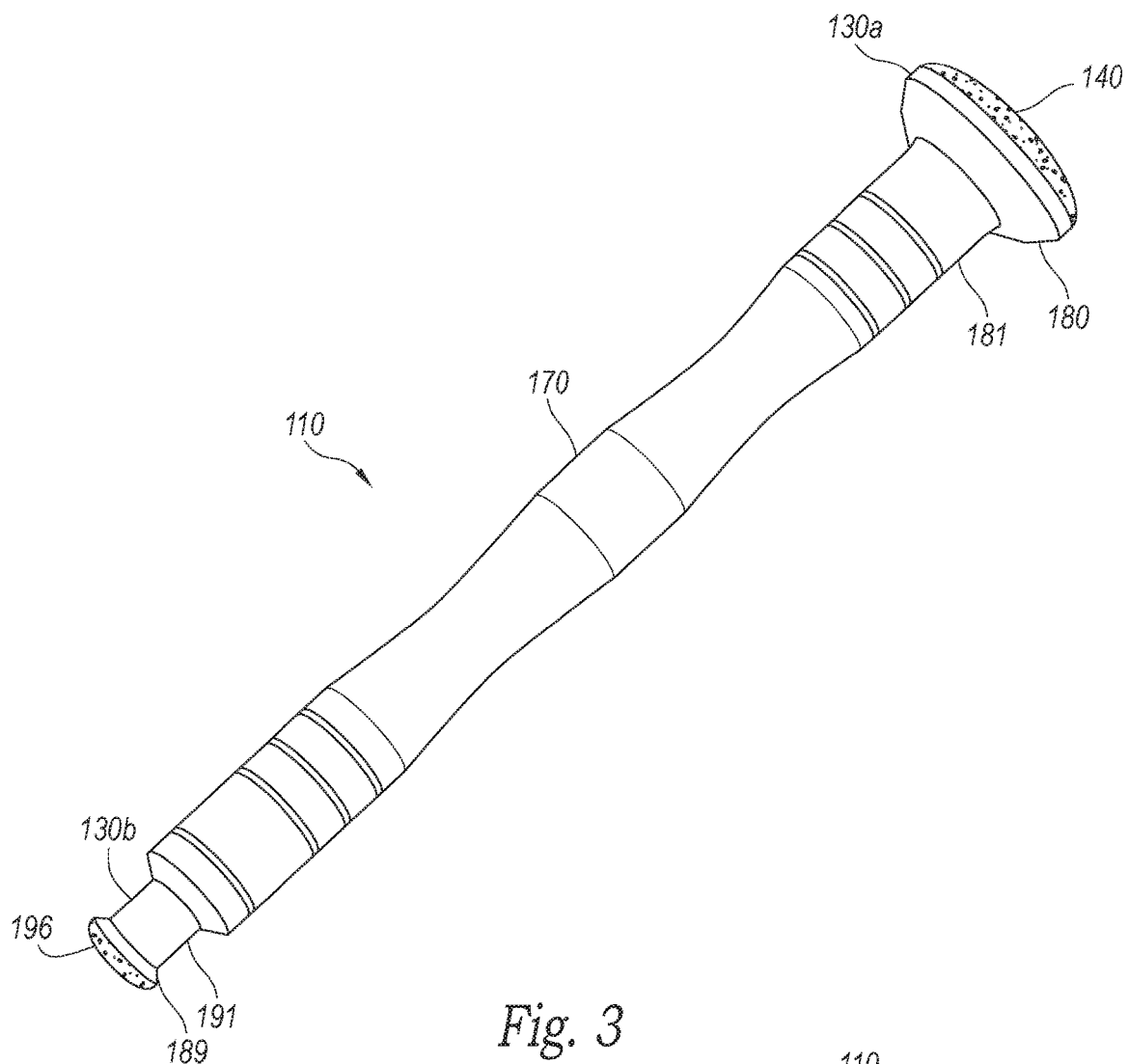
FIG. 3 is an isometric view of a microdermabrasion wand in accordance with an embodiment of the technology.
Figure 4:
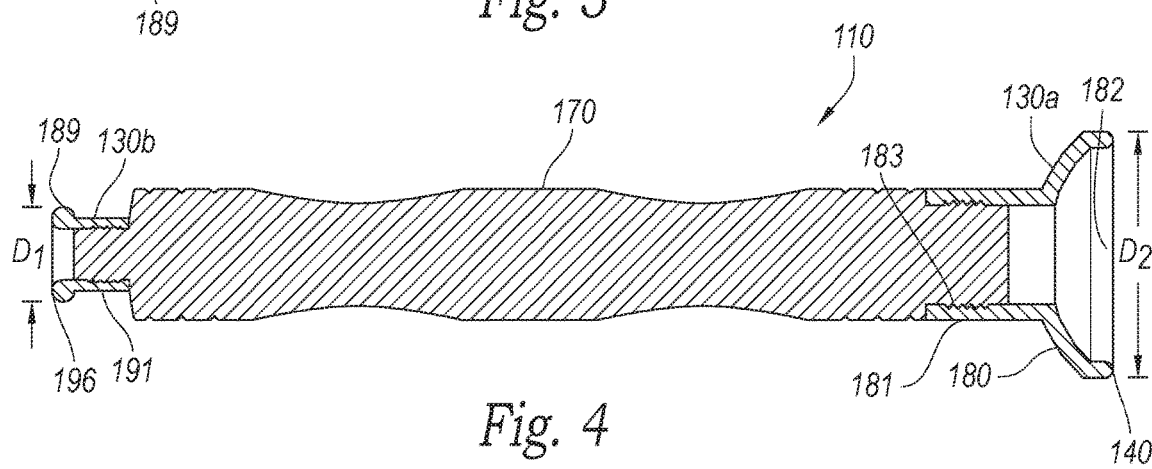
FIG. 4 is a cross-sectional view of the microdermabrasion wand of FIG. 3.

FIG. 3 is an isometric view of the microdermabrasion wand 110 in accordance with an embodiment of the technology. FIG. 4 is a cross-sectional view of the microdermabrasion wand 110 of FIG. 3. Referring now to FIGS. 3 and 4, the description of the abrasive tip 130a applies equally to the abrasive tip 130b, unless indicated otherwise. The abrasive tip 130a can include a head 180 and a body 181. The head 180 can include the contact region 140 defining opening 182 (FIG. 4) into which the skin can be received when the contact region 140 is pressed against the patient. The contact region 140 can be an annular abrasive region. In other embodiments, the contact region 140 can have a substantially elliptical shape, rounded polygonal shape, or the like. The body 181 can include, without limitation, a generally tubular body and one or coupling features, such as internal threads 183 (FIG. 4).

The abrasive tip 130b can include a head 189 and a body 191. The head 189 is smaller than the head 180 of the abrasive tip 130a. As shown in FIG. 4, a diameter $D_1$ defined by a contact portion 196 of the head 189 is smaller than the diameter $D_2$ defined by the contact portion 140. The abrasive tip 130b can be used on highly contoured and/or relative small treatment sites. For example, the abrasive tip 130b can be used along a subject's nose whereas the abrasive tip 130a can be used along the subject's back. In some embodiments, the mechanical characteristics of the contact region 196 is the same as or substantially similar to contact region 140. The mechanical characteristics can include, without limitation, surface roughness, shape, curvature, surface area, grit, combinations thereof, or the like.

Figure 5:
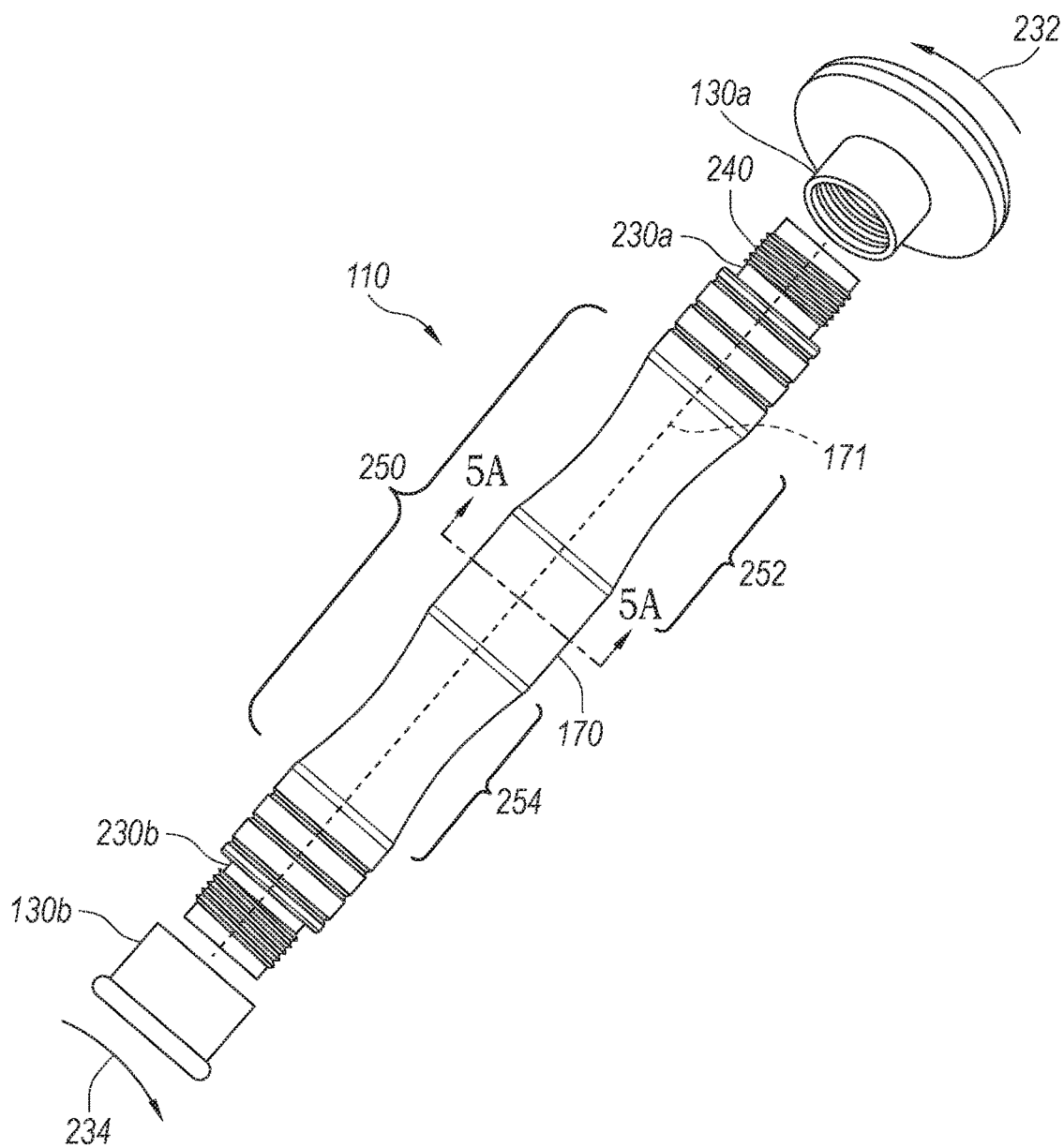
FIG. 5 is an exploded isometric view of a microdermabrasion wand in accordance with an embodiment of the technology.

FIG. 5 is an exploded isometric view of the microdermabrasion wand 110 in accordance with one embodiment. In some embodiments, the main body 170 is symmetrical about its longitudinal axis 171. The wand main body 170 can include opposing ends 230a, 230b configured to be coupled to the abrasive tips 130a, 130b, respectively. The description of the end 230a applies equally to the end 230b, unless indicated otherwise. In some embodiments, the tip 130a can be rotated in a clockwise direction, as indicated by arrow 232, to be coupled to the end 230a. The installed tip 130a can be rotated in the opposite counterclockwise direction to remove it from the end 230a. In this manner, a user can rapidly replace abrasive tips without permanently damaging the tips and/or wand main body 170. In a treatment session, any number of tips can be utilized.

The end 230a can include interface elements or coupling features 240 for engaging the abrasive tip 138. The coupling features 240 can include, without limitation, connection elements, threads (e.g., external threads, threaded surfaces, etc.), protrusions, or the like. In some embodiments, the abrasive tip 130a has internal threads that threadably couple to the end 240 via the external threads 240. In other embodiments, the abrasive tip 130a can be magnetically coupleable to the end 230a. For example, the abrasive tip 130a and/or end 230a can include one or more magnets. In other embodiments, a mechanical fastener (e.g., a pin) can detachably couple the abrasive tip 130a to the end 230a. The ends 230a, 230b can be geometrically congruent such that tips can be applied on either end. The dimensions and configurations of the abrasive tips 130a, 130b and ends 230a, 230b can be selected based on the microdermabrasion procedure to be formed.

Figure 5A:
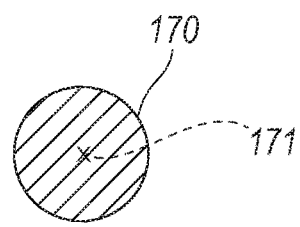
FIG. 5A is a cross-sectional view taken along line 5A-5A of FIG. 5.

FIG. 5A is a cross-sectional view taken along line 5A-5A of FIG. 5. The wand body 170 has a longitudinal length and a substantially solid cross-section along most of the longitudinal length. In some embodiments, the wand body 170 has a solid-cross section taken generally perpendicular to its longitudinal axis. In one embodiment, the wand body 170 has a solid traverse cross section without any vacuum passageways (e.g., lumen, hoses, etc.). The wand body 170 can be made, in whole or in part, of one or more metals, plastics, or other rigid materials. In one embodiment, the wand body 170 comprises stainless steel, aluminum, or combinations thereof.

Figure 6:
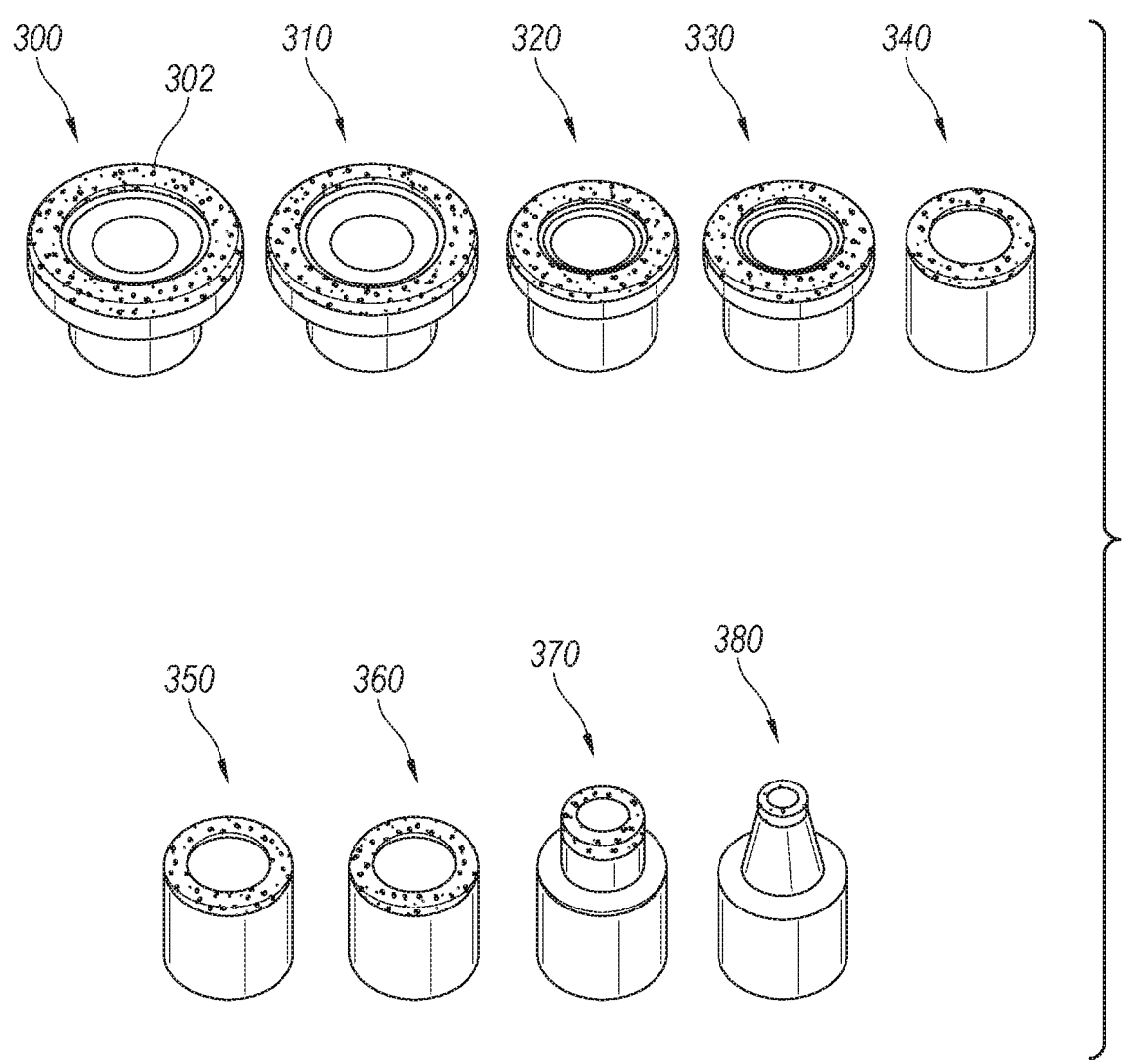
FIG. 6 shows an array of treatment tips in accordance with embodiments of the technology.

FIG. 6 shows an array of treatment elements in the form of abrasive tips in accordance with embodiments of the technology. The tips can have the same or varying degrees of roughness. Rougher tips can be used for coarser treatment areas whereas less rough tips can be used for sensitive treatment areas. An abrasive tip 300 has a large contact region or portion 302 for abrading relatively large treatment areas, such as the chest, arms, legs, or feet. The contact portion 302 can include one or more abrasive materials, including diamond, aluminum oxide, sand, silicon carbide, and/or silicon oxide. The abrasive material can be coupled (e.g., adhered, bonded, fused, etc.) or integrated into the tip. For example, crystals in 60 grit, 80 grit, 100 grit, 120 grit, 150 grit, or 200 grit can be adhered to a tip surface. Aluminum oxide of about 100 grit can remove a relatively large amount of cells to provide an aggressive treatment whereas aluminum oxide of about 150 grit can remove a relatively low amount of cells. The tip 300 can have a relatively low grit (e.g., 100 grit) to aggressively treat large areas, and the tips 360, 370, 380 can have relatively high grits (e.g., 200 grit or higher) to polish or treat sensitive areas. In other embodiments, the contact portion is formed via a cutting process, stamping, or the like. The fine tip 380 can be used on sensitive areas, such as the face and neck. Abrasive tips 310, 320, 330, 340, 350, 360, 370, 380 can have progressively smaller configurations. The configurations, number, and abrasion characteristics of the tips can be selected based on the treatment protocols.

Figure 7:
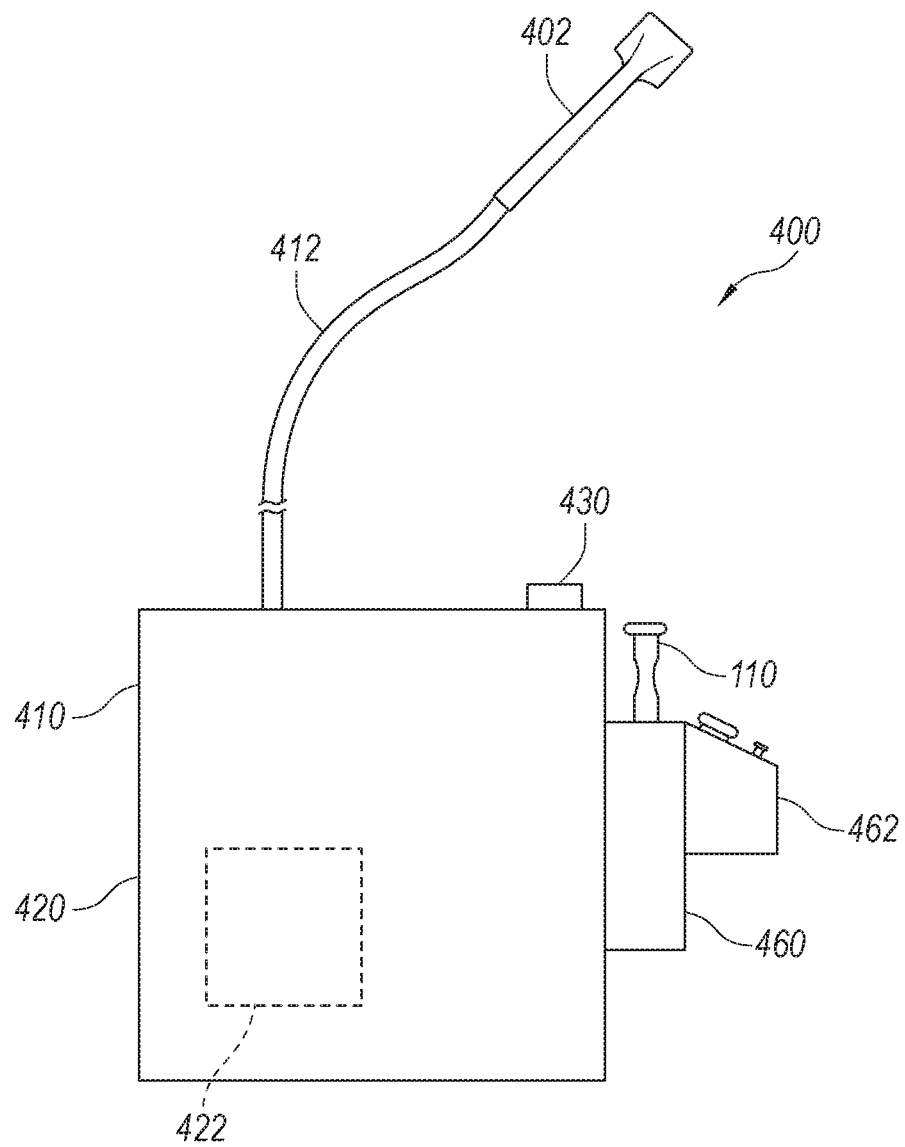
FIG. 7 is a schematic view of a vacuum apparatus in accordance with one embodiment of the technology.

FIG. 7 shows a vacuum apparatus 400 in accordance with one embodiment. The vacuum apparatus 400 can include a vacuum wand 402, a console unit 410, and a conduit 412. The console unit 410 can include a main body 420 that houses one or more internal components, such as a pressurization device 422 (shown in phantom line), sensors, filters, collection containers, and other components suitable for use with vacuum systems. A control element 430 can be used to adjust operation. If the vacuum level is too high, undesirable patient discomfort and/or tissue damage could occur. Accordingly, the control element 430 can be used to reduce the vacuum to an appropriate level. A vacuum level can be selected based on the characteristics of the tissue and desired level of comfort. In some embodiments, the control element 430 is a dial. In other embodiments, the control element 430 can be a controller that includes, without limitation, one or more processors, memory, executable instructions, and software. In further embodiments, the control element 430 can include one or more switches or toggles that turn the pressurization device 422 OFF and ON.

The pressurization device 422 can draw a vacuum level of about 10, 20, 30, 40, 50, 60, 70, or 80 cmHG. Other vacuum levels can be used if desired. If the vacuum level is too low, the wand 118 may not be adequately held, clean, or manipulate the tissue. If the vacuum level is too high, undesirable discomfort to the subject and/or tissue damage (including bruising) could occur. The control element 430 can control the vacuum level to draw tissue into the vacuum wand 402 while maintaining a desired level of comfort. In some embodiments, air pressure can be controlled by a regulator located between the pressurization device 422 and the vacuum wand 402. The configuration, components, and operation of the console unit 410 can be selected based on the desired pressure levels, skin cleaning capabilities, and other treatment parameters.

The console unit 410 can further include a wand holder 460 and/or tip holder 462. The wand holder 460 is configured to hold one or more microdermabrasion wands 110. In some embodiments, the holder 460 can have openings configured to hold an array of different sized microdermabrasion wands. In other embodiments, the holder 460 is configured to hold a single microdermabrasion wand. In some embodiments, the vacuum apparatus 422 is configured to support multiple wands at the same time. This allows multiple wands be used to concurrently perform microdermabrasion procedures on different subjects. The tip holder 462 can hold one or more abrasive tips, such as the array of tips shown in FIG. 6. The position, configuration, and holding capacity of the holder 460 can be selected based on the number of wands to be used, procedures to be performed, and treatment flexibility.

The console unit 410 can further include one or more power supplies, controllers, fluidic components (e.g., valves, manifolds, etc.), holders (e.g., bottle holders), optical equipment (e.g., magnifying lamps), light sources (e.g., LED lights, Wood's lamp, etc.), heaters, and combinations thereof. For example, the console unit can include, or be configured for use with brushes (e.g., massage brushes), exfoliating tools, hair removal devices, hot towel cabinets, topical substances (e.g., skin gels), or the like.

Figures 8, 9:
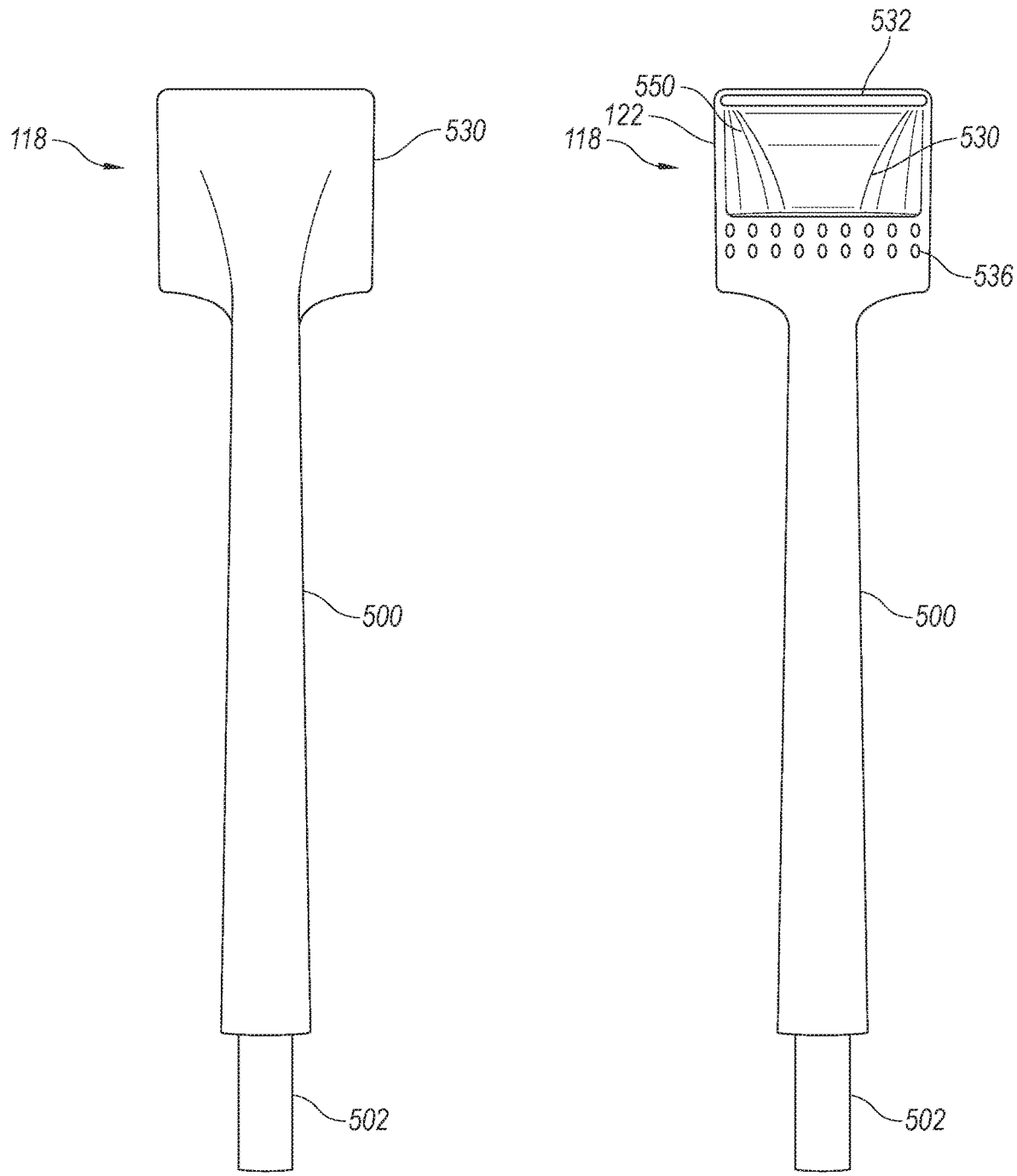
FIG. 8 is a top view of a vacuum skin holder wand in accordance with an embodiment of the technology.
FIG. 9 is a bottom view of a vacuum skin holder wand in accordance with another embodiment.
Figure 10:
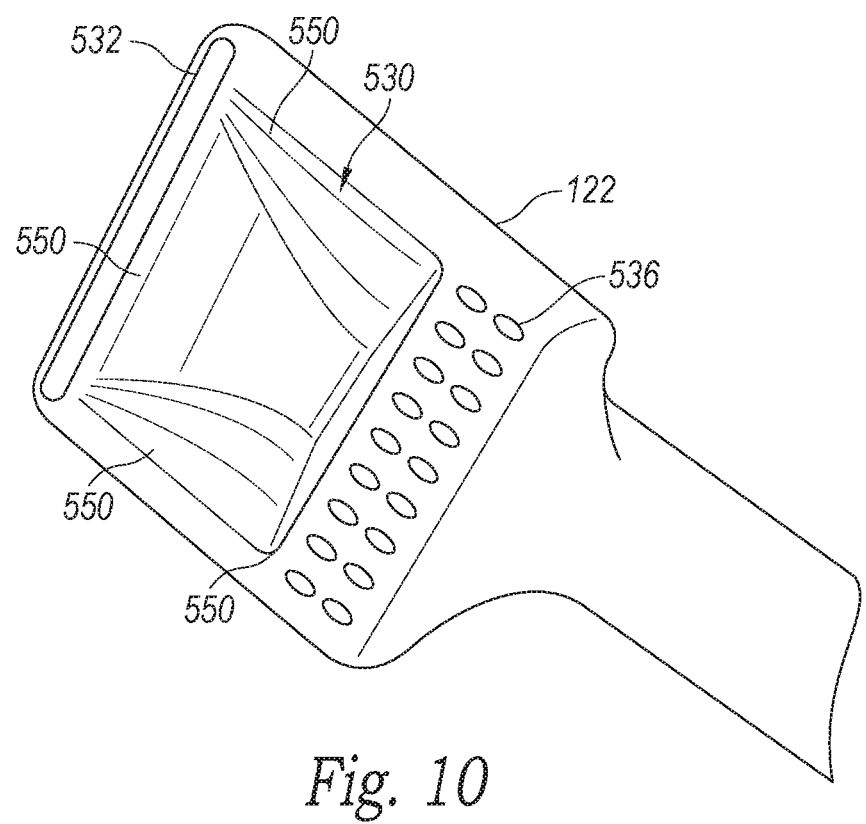
FIG. 10 is an isometric view of a head of the vacuum skin holder wand of FIG. 8.
Figure 11:
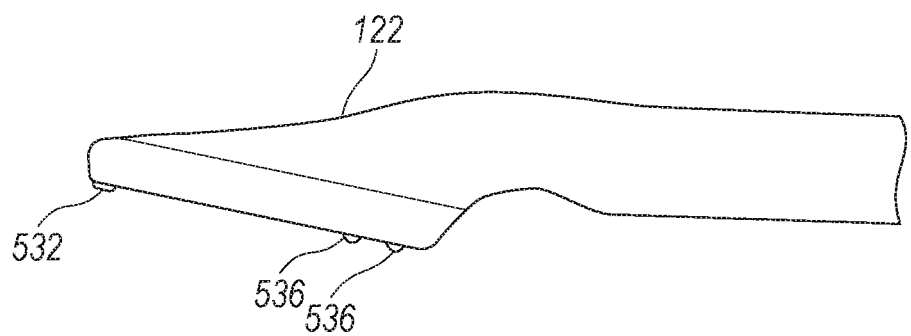
FIG. 11 is a side view of the head of the vacuum skin holder wand of FIG. 8.

FIG. 8 is a plan view of the vacuum wand 118 in accordance with an embodiment of the technology. FIG. 9 is a bottom view of the vacuum wand 118 of FIG. 8. FIGS. 10 and 11 show the head 122 of the vacuum wand 118.

Referring now to FIGS. 8 and 9, the vacuum wand 118 can include an elongate handle 500 and a connector 502. The elongate handle 500 can be sufficiently long to be comfortably gripped by a user. The connector 502 extends from the elongate handle 500 and can be coupled to a conduit, such as a conduit 123 of FIG. 1. The connector 502 can include, without limitation, a narrowed region, sealing members (e.g., O-rings), other suitable features for engaging the conduit 123.

Referring now to FIGS. 9 and 10, the head 122 defines an entrance or inlet port 530 and includes an engagement feature 532 and an array of contact features 536 (one labeled in FIGS. 9 and 10). The entrance 530 is in the form of an opening toward or into which skin can be comfortably drawn. When the head 122 is applied to the skin, a vacuum can be drawn to pull skin gradually toward or into the opening 530. Contoured smooth surfaces 550 (FIG. 9) surrounding the opening 530 allow the skin to slide smoothly into the head 122. In some embodiments, the opening 530 can have a generally rectangular shape. In other embodiments, the opening 530 has a generally elliptical shape, rounded shape, or the like. For example, an elliptical opening 530 can be used to overlay facial skin adjacent to patient's eye.

The engagement feature 532 can include an elongated grip-strip configured facilitate gripping skin and can be made, in whole or in part, of rubber, silicon, plastic, combinations thereof, or other materials suitable for limiting, inhibiting, or preventing unwanted movement of the head 122 relative to the subject's skin. The configuration and materials of the engagement feature 532 can be selected based on the desired frictional interaction and patient comfort. The engagement features 536 can include, without limitation, protrusions, bumps, recesses, or other suitable features for providing desired interaction with the subject's skin, as discussed in connection with FIGS. 12A-12D.

FIGS. 12A-12D illustrate stages of one method of treating a subject. Generally, an abrasive wand can mechanically alter a subject's skin. The head 122 of the vacuum wand 118 can be applied to the skin 116 to inhibit, limit, or substantially prevent movement of the skin. Abrasive tips of the abrasive wand can be replaced, multiple abrasive wands can be used in a session, and a skin holding wand can be used to inhibit movement of the subject's skin. Details of the methods of treatment are discussed in connection with FIGS. 12A-12D.

Figure 12A:
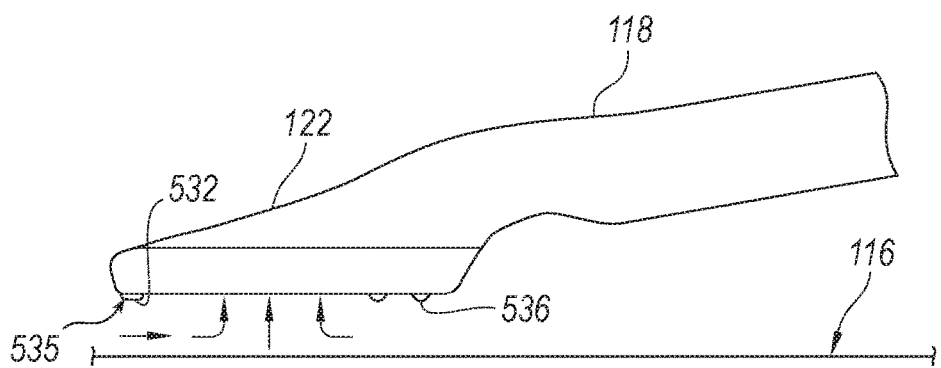
FIGS. 12A-12D illustrate stages for one method of treating a subject.

FIG. 12A is a side view of the head 122 ready to be applied to the skin 116. The engagement feature 532 has a subject-contact surface 535 positioned to contact the skin 116 when the head 122 holds the subject's skin under vacuum. The subject-contact surface 535 can be an arcuate surface, a curved surface, a non-planar surface, or the like. A vacuum can be drawn to draw air into the head 122, as indicated by the arrows. In some procedures, the vacuum can be drawn before applying the head 122. In other embodiments, the vacuum can be drawn during or after application of the head 122 to the skin.

Figure 12B:
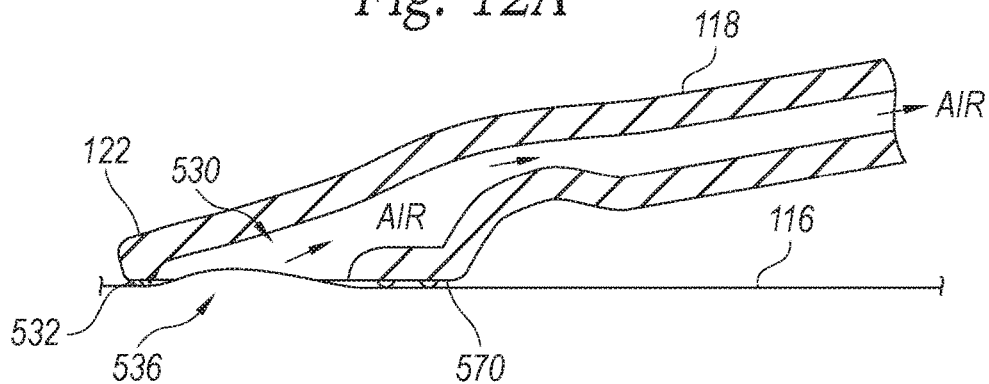

FIG. 12B is a cross-sectional view of the head 122 applied to the subject. A region of skin 536 has been pulled into the opening 530. The vacuum level can be increased or decreased to increase or decrease the volume of tissue located inside of the head 122. The engagement member 532 can remain in contact with the surface of the skin 116. To break the seal (e.g., an substantially air-tight seal), the vacuum wand 118 can be rotated or lifted away from the subject. In other embodiments, the vacuum wand 118 can hold the subject's tissue by continually drawing air through the head 122 without forming an airtight seal.

Figure 12C:
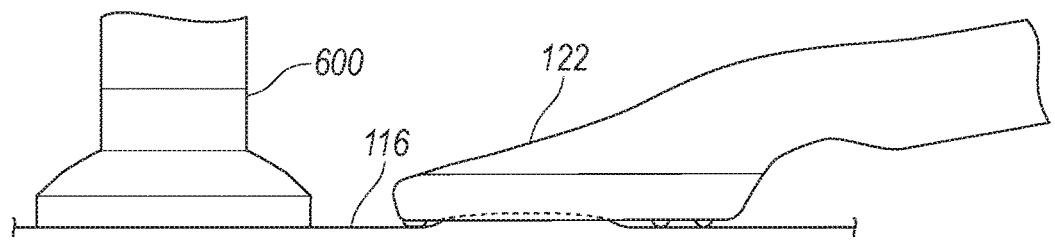
Figure 12D:
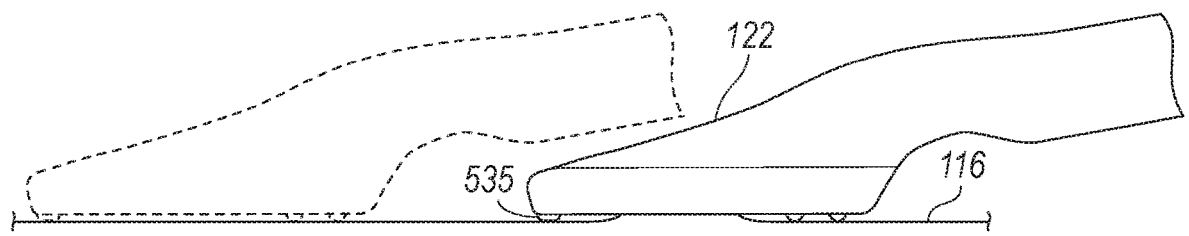

FIG. 12C is a side view of an abrasive tip 600 of a microdermabrasion wand applied to the skin 116. The tip 600 can be moved across the skin 116 while providing a desired level of pressure (e.g., a constant pressure, a varying pressure, etc.). The pressure can be selected based on the desired abrasion, level of comfort, or other treatment parameters. The head 122 can remain generally stationary relative to the skin or can be repositioned any number times during one or more treatment sessions. The abrasive tip 600 can be any one of the abrasive tips discussed herein. The abrasive tip and another abrasive tip installed on a wand body can be used to sequentially abrade skin. In some procedures, the head 122 can securely hold a region of the subject's skin that is larger than an area skin being contacted by the abrasive tips. The large contact region can help prevent discomfort or pain. The size, configuration, and contact interface between the head 122 to the patient can be selected based on the desired holding capabilities After treatment has been completed, the head 122 can be moved to another location, as shown in phantom line in FIG. 12D. The subject-contact surface 535 can facilitate smooth, comfortable movement along the skin 116. The head 122 can draw a sufficient vacuum to securely hold a region of the subject's skin while the abrasive tip 600 is moved along an adjacent region of the subject's skin to perform a microdermabrasion procedure.

Figure 13:
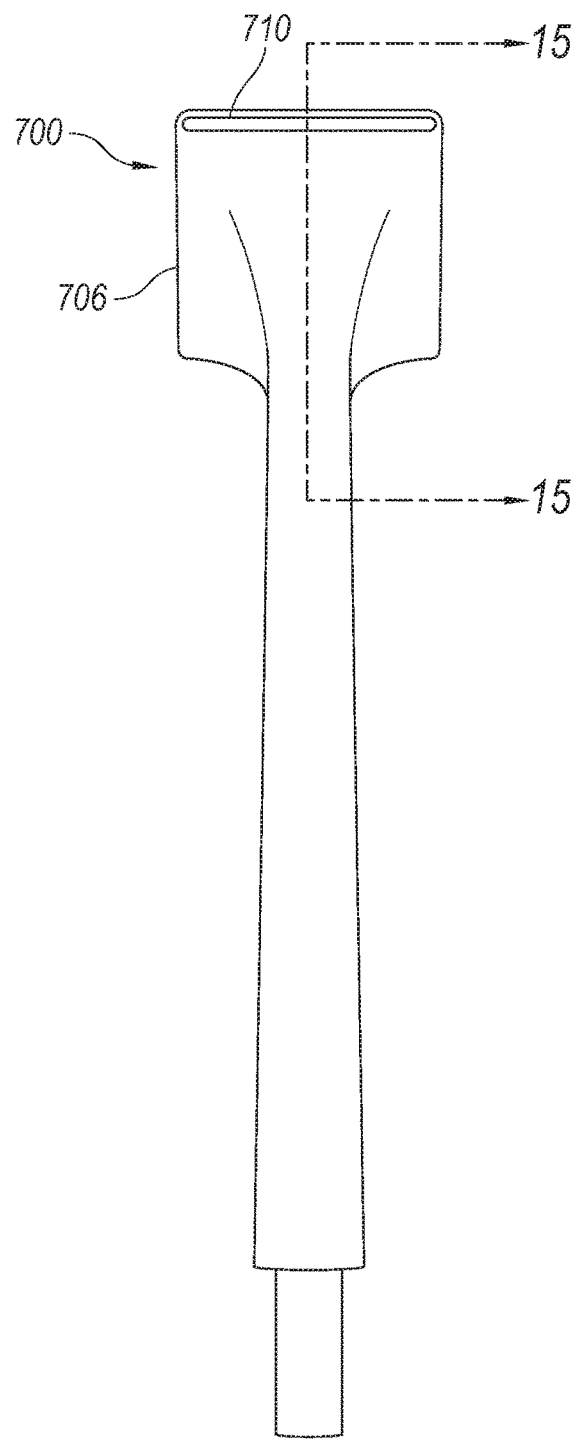
FIG. 13 is a top view of a vacuum skin holder wand with a removable engagement feature.
Figure 14:
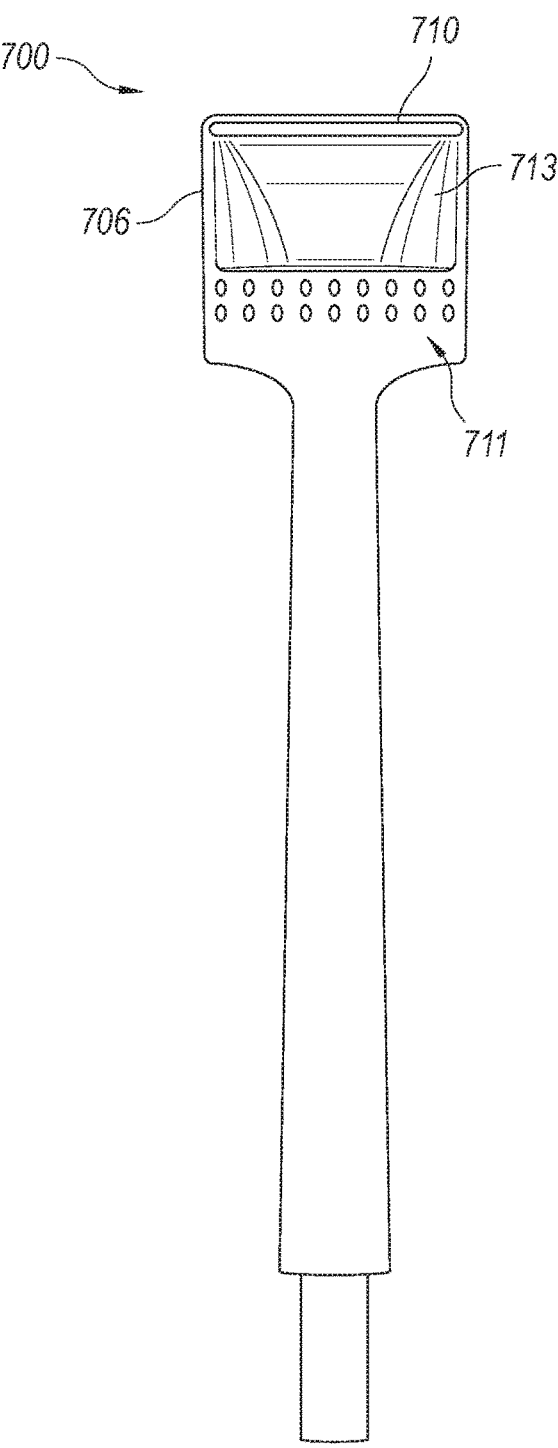
FIG. 14 is a bottom view of the vacuum skin holder wand of FIG. 13.

FIG. 13 is a top view of a vacuum wand 700 with a head 706 and a removable engagement feature 710. FIG. 14 is a bottom view of the vacuum wand 700. The description of the vacuum wands 118, 402 applies equally to the vacuum wand 700 unless indicated otherwise.

The engagement feature 710 can be a compliant member configured to facilitate treatment by, for example, gripping and tightening the skin to enhance manual dermabrasion. The engagement feature 710 can include texturing, protrusions, dimples, and/or combinations thereof for providing desired interaction with the skin. For example, the engagement feature 710 can be a compliant strip that can be replaced to provide one or more benefits, including, but not limited to, convenient cleaning, facilitate sanitation and sterilization, or replacement when worn. The engagement feature 710 can be replaced with another engagement feature in the same session or different treatment session. A user can replace the engagement feature any number of times during a treatment session to tailor the session to a particular subject.

The wands disclosed herein can have any number of engagement features. In some embodiments, wands can have engagement features on opposite sides of the vacuum port. For example, the contact features 711 of FIG. 14 can be replaced with a single engagement feature similar to the illustrated engagement feature 710. In other embodiments, each side of the vacuum port 713 can be surrounded by contact features. In yet another embodiment, the engagement feature 710 in FIG. 14 can be replaced with one or more contact features 711. For example, an array of regularly or irregularly spaced contact features can be positioned on multiple sides of the vacuum port 713.

Figure 15:
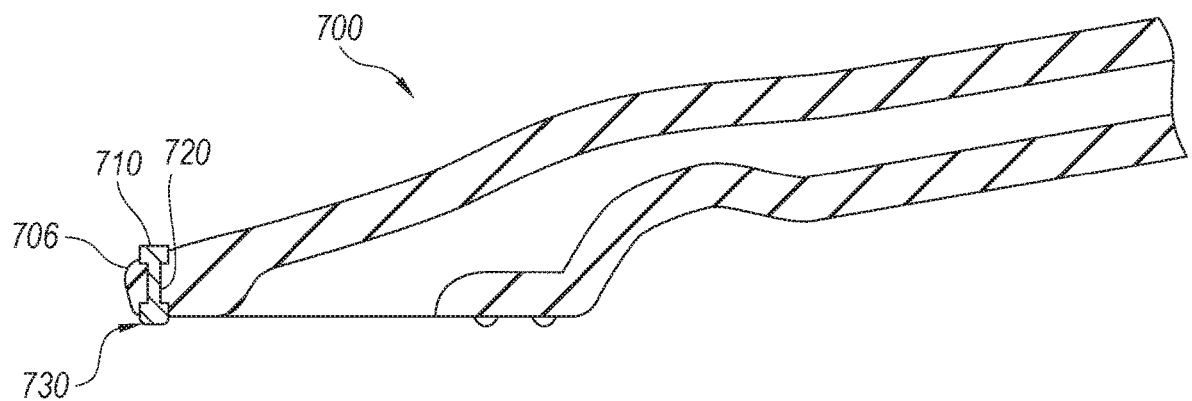
FIG. 15 is a cross-sectional view taken along line 15-15 of FIG. 13.

FIG. 15 is a cross-sectional view taken along line 15-15 of FIG. 13. The engagement feature 710 can be removably coupled to an opening or window 720 (shown empty in FIG. 16) in the head 706 and can be made, in whole or in part, of one or more compliant materials, such as silicon, rubber, polymers, and or the like. In multilayer embodiments, the engagement feature 710 can have a plurality of separate layers, each with a characteristic selected to enhance treatment. The configuration, composition, and characteristics of the engagement feature 710 can be selected based on the procedure to be performed. To enhance tissue-gripping capabilities, the engagement feature 710 can include a high-friction or abrasive surface 730. In other embodiments, the surface 730 can be a low-friction surface that allows sliding along skin.

Figure 16:
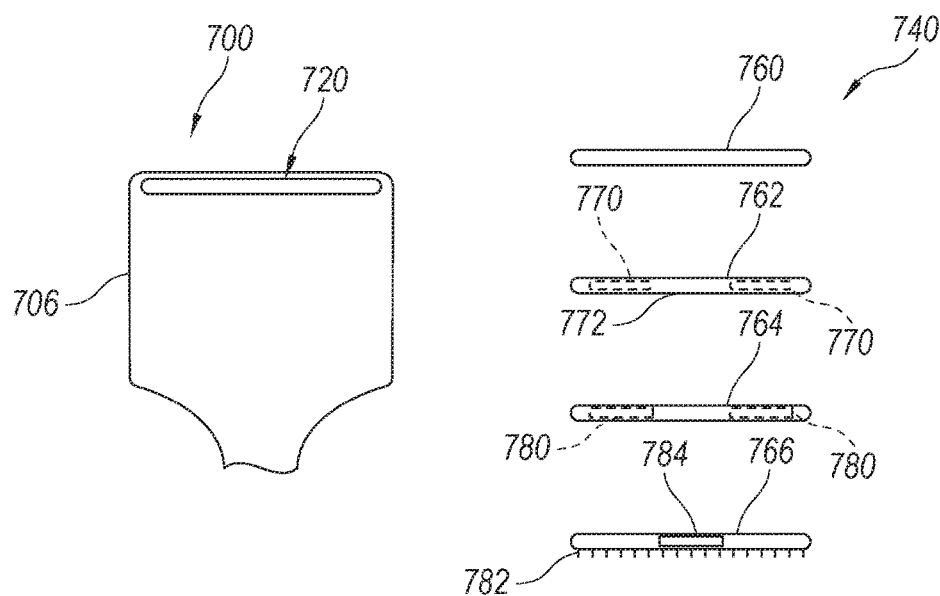
FIG. 16 illustrates a head of a vacuum skin holder wand and a set of engagement features in accordance with an embodiment of the technology.

FIG. 16 illustrates the vacuum wand 706 and a set 740 of engagement features in the form of compliant strips 760, 762, 764, 766. The set 740 can include any number of strips that are geometrically congruent for interchangeability, and sets can be selected based on the procedure to be performed. The description of the engagement feature 710 of FIGS. 13 to 15 applies equally to the strip 760 of FIG. 16. The engagement strips 762, 764, 766 can have other characteristics and configurations with one-piece or multi-piece constructions. By way of example, the strip 762 can include one or more nodes/protrusions 770 (illustrated in dashed line) for providing a massage effect. The protrusions 770 can be integrally formed with a main body 772 of the strip 762.

The strip 764 can include one or more energy-emitting elements 780 capable of providing energy. The energy-emitting elements 780 can be, for example, light sources, massaging elements, electrodes, thermal elements, acoustic emitters, or the like. Light sources can include, without limitation, light-emitting diodes, laser sources, fiber optics, or combinations thereof. Massaging elements can be mechanical elements capable of providing mechanical energy, such as pulsation, vibration, or ultrasound. Electrodes can include radio frequency electrodes capable of delivering RF energy to the subject's skin. Thermal elements can include, without limitation, Peltier devices, resistive heaters, cooling channels (e.g., channels through which a chilled fluid flows), or the like. The energy-emitting elements 780 can have an internal power source, such as one or more batteries. In other embodiments, an external power source can be electrically coupled to the elements 780.

FIG. 16 shows a side view of the strip 766 with a brush 782 for cleaning a subject's skin, spreading topically applied substances (e.g., gels, lotions, etc.), mechanically agitating skin, or combinations thereof. In other embodiments, the strip 766 can include one or more pads, abraders, or the like.

The wands disclosed herein can include one or more sensing elements for monitoring treatment. The engagement feature 766 of FIG. 16 can include a sensing element 784 that can include, without limitation, one or more pressure sensors, temperature sensors, optical skin analyzers, or the like. Signals from the sensing element 784 can be used to control operation of the wand 700 or other components of a system. In other embodiments, one or more sensor elements can be incorporated into the reusable wand heads.

Figure 17:
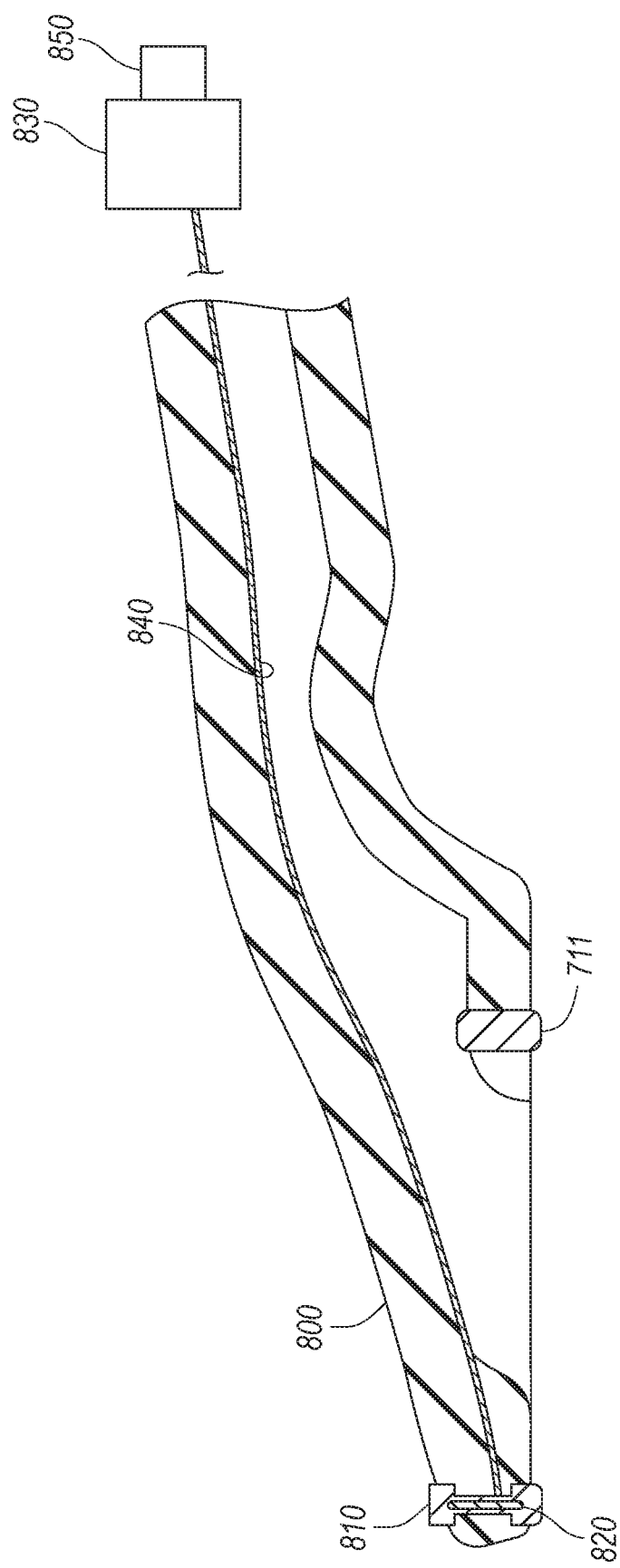
FIG. 17 is a cross-section view of a vacuum head in accordance with one embodiment.

FIG. 17 is a cross-sectional view of a head of a vacuum wand in accordance with another embodiment. The vacuum head 800 is generally similar to the vacuum head 706 discussed in connection with FIGS. 13-16, except as indicated otherwise. The vacuum head 800 has an engagement feature 810 that includes an energy-emitting element 820 in communication with console unit 830 via a line 840. The line 840 can include one or more wires that provide electrical communication between the energy-emitting element 820 and the console unit 830.

The console unit 830 can include a controller 850 with instructions to perform the treatment profiles and/or patient-specific treatment routine, which can include one or more segments, and each segment can include vacuum levels, energy emitting protocols, and/or specified durations (e.g., 30 seconds, 1 minute, 2 minutes, 3 minutes, etc.). Visual or audible alerts can be provided to an operator to notify the operator that, for example, suitable abrasion of a specific treatment area has been achieved, the engagement feature 810 should be replaced, or other information.

The conduits disclosed herein can include one or more electrical lines for providing power to features of the wands and/or one or more control lines for providing communication between the control wands and a console unit. Electrical lines can provide power to energy emitting elements, sensors, and so forth. Control lines can provide communication between sensing elements and console unit. In various embodiments, the conduits (e.g., conduit 123 of FIG. 1) can be the form of a connector with a bundle of conduits, power lines, wired connections, vacuum lines, or other bundled and/or unbundled components selected to provide desired functionality. The number, configurations, and features of the conduits can be selected based on the treatment to be performed.

Treatment sessions can be equal to or shorter than 2 hours, 1 hour, 45 minutes, 30 minutes, or 10 minutes. A number of sessions (e.g., 4, 5, 6, 7, 8, 9, or 10 sessions) can be performed at particular intervals (e.g., 3 days, 5 days, 10 days, 15 days, etc.). In some protocols, the intervals between sessions can be 1-15 days, 3-12 days, 5-11 days, or 7-10 days. In one treatment program, six sessions can be performed about 7 to 10 days apart. The number of sessions, lengths of sessions, and level of abrasion can be selected based on the treatment goals, such as treating wrinkles, pigmentation abnormalities, or the like. Substances can be applied to the treatment site before, during, or after performing microdermabrasion. Before treatment, cleaners, toners, and pretreatment substances (e.g., gels) can be applied to the skin. During treatment, cleaners and/or moisturizers can be periodically applied. After treatment, cosmetic skin care compositions can be applied to, for example, promote cell growth in the underlying dermis. Some non-limiting examples of cosmetic skin care compositions include skin creams, moisturizers, lotions, or the like. The vacuumless handpieces can be used with gels and substances without clogging fluid lines and without consuming abrasive material.

The methods disclosed herein can exfoliate skin to improve the appearance of skin, remove skin abnormalities, and otherwise treat skin. In some procedures, the treatments can produce skin care benefits, including improving skin appearance, enhancing the feel of the skin (e.g., producing a smoother, more even appearance and/or feel), increasing the thickness of one or more tissue layers (e.g., epidermis, dermis, etc.), altering the elasticity and/or resiliency of the skin, altering the firmness of the skin (e.g., increasing skin firmness), altering the appearance of fine lines and/or wrinkles (e.g., by reducing the visibility of lines/wrinkles), improving skin texture, combinations thereof, etc. The methods can include one or more treatment protocols selected based on the desired skin care benefits. Non-limiting exemplary treatment protocols include, without limitation, pretreatment routines (e.g., application of lotions, topical substances, or the like), post treatment routines, abrasion routines, or the like. In a single treatment, multiple treatment protocols can be combined. For example, a pretreatment routine can prepare the skin for exfoliation. An aggressive abrasion routine can be performed on certain areas. A moderate aggressive abrasions routine can be performed at those areas and other areas.

Aspects of the described technology can be modified, if necessary, to employ the systems, functions, and concepts of the various references described above to provide yet further embodiments. The descriptions of the vacuum apparatuses 112, 420 applies equally to one another, unless indicated otherwise. Additionally, the systems, components, and methods disclosed herein can be used to perform a wide range of procedures, including skin cleaning, skin texturing (with or without microdermabrasion), treating acne, or the like. Handpieces and vacuum apparatuses disclosed herein can be used alone or with one another. Controllers can include one or more processors, a memory, input/output devices, and/or subsystems and other components. Processors can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices. In various embodiments, the memory can be flash memory, secure serial EEPROM, secure field programmable gate array, or secure application-specific integrated circuit.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. The systems, features, and methods disclosed herein can be combined or used with the systems, features, and methods disclosed in U.S. Provisional Patent Application No. 62/426,165, filed Nov. 23, 2016 and U.S. Patent Application No. 62/453,934, filed Feb. 23, 2017, which are incorporated by reference in their entireties.

While the above description details certain embodiments and describes the best mode contemplated, no matter how detailed, various changes can be made. Implementation details may vary considerably, while still being encompassed by the technology disclosed herein. The various aspects and embodiments disclosed herein are for purposes of illustration and are not intended to be limiting, with the true scope and spirit being indicated by the following claims.

What is claimed is:

1. A microdermabrasion system, comprising:
   a microdermabrasion wand having a first abrasive tip, a second abrasive tip, and a wand body having a proximal end and a distal end, the first and second abrasive tips are configured to be coupled to the proximal and distal ends, respectively;
   a console unit including a wand holder and a pressurization device, wherein the pressurization device is configured to draw a vacuum; and
   a skin holder assembly including a suction wand and a conduit connecting the suction wand to the pressurization device, wherein the pressurization device is configured to draw a sufficient vacuum to cause the suction wand to hold a subject's skin to inhibit movement of skin contacting while the first abrasive tip moves along the skin relative to the suction wand.

2. The microdermabrasion system of claim 1, wherein the microdermabrasion wand is a vacuumless wand, and the suction wand is configured to securely hold a first region of the subject's skin via the vacuum while the first abrasive tip is moved along an adjacent second region of the subject's skin to perform at least a portion of a microdermabrasion procedure.

3. The microdermabrasion system of claim 1, wherein the suction wand includes a head and an engagement feature detachably coupled to the head, wherein the head includes a vacuum port, and wherein the engagement feature has a subject-contact surface positioned to contact the subject's skin when the head holds the subject's skin under vacuum via the vacuum port.

4. The microdermabrasion system of claim 1, wherein the wand body has a longitudinal length and a substantially solid cross-section along most of the longitudinal length.

5. The microdermabrasion system of claim 1, wherein the first abrasive tip is detachably coupled to a first end of the wand body, and the second abrasive tip is detachably coupled to a second end of the wand body.

6. The microdermabrasion system of claim 5, wherein the first end threadably couples to the first abrasive tip.

7. The microdermabrasion system of claim 1, wherein the wand body has a solid cross section along substantially all of its longitudinal length.

8. The microdermabrasion system of claim 1, wherein the wand body includes a handle portion configured to be manually gripped by a user.

9. The microdermabrasion system of claim 1, wherein the console unit includes one or more pressurization devices for drawing the vacuum.

10. The microdermabrasion system of claim 1, wherein the suction wand includes a replaceable strip, the replaceable strip is configured to contact the subject's skin when the suction wand holds the subject's skin.

11. The microdermabrasion system of claim 10, wherein the replaceable strip includes one or more massaging features and/or energy-emitting elements.

12. The microdermabrasion system of claim 1, wherein the suction wand defines a tissue-receiving reservoir configured to receive the subject's tissue under vacuum.

13. A microdermabrasion system, comprising:
   a vacuumless microdermabrasion wand having at least one abrasive tip;
   a skin holder assembly including a suction wand configured to hold a subject's skin taught while the vacuumless microdermabrasion wand abrades the subject's skin, the skin holder including a head, wherein the head includes an opening configured to receive the subject's skin, and
   engagement features located on opposite sides of the opening, the engagement features are protrusions, bumps, and/or recesses configured to facilitate gripping of the subject's skin when the skin is drawn into the opening;

a console unit including
a pressurization device configured to be fluid communication with the skin holder assembly and operable to draw air through the suction wand, and wherein the pressurization device includes one or more vacuum pumps; and a control element that controls operation of the pressurization device such that the pressurization device operates to provide a sufficiently low pressure to hold a subject's skin against the suction wand to inhibit movement of skin relative to the suction wand while the vacuumless microdermabrasion wand is used to perform at least a portion of a microdermabrasion procedure.

14. The microdermabrasion system of claim 13, wherein the control element includes one or more dials, switches, and/or toggles that turn the pressurization device off and on.

15. The microdermabrasion system of claim 13, wherein the console unit includes a fluid line coupling the pressurization device to the skin holder assembly.

16. The microdermabrasion system of claim 13, wherein the microdermabrasion wand includes a solid main body with a solid-cross section taken substantially perpendicular to a longitudinal axis of the solid main body.

\* \* \* \* \*